United States Patent
Bjorum et al.

(10) Patent No.: US 11,872,353 B2
(45) Date of Patent: Jan. 16, 2024

(54) STORAGE APPARATUS FOR ELONGATE ARTICLES

(71) Applicant: Raspberry Med, Inc., Grand Rapids, MI (US)

(72) Inventors: Justin M. Bjorum, Wyoming, MI (US); Noel J. Bodkins, Ada, MI (US)

(73) Assignee: Raspberry Med, Inc., Grand Rapids, MI (US)

( * ) Notice: Subject to any disclaimer, the term of this patent is extended or adjusted under 35 U.S.C. 154(b) by 661 days.

(21) Appl. No.: 17/025,451

(22) Filed: Sep. 18, 2020

(65) Prior Publication Data

US 2021/0077773 A1 Mar. 18, 2021

Related U.S. Application Data

(60) Provisional application No. 62/901,941, filed on Sep. 18, 2019.

(51) Int. Cl.
*A61M 25/00* (2006.01)
*A61M 29/00* (2006.01)
(Continued)

(52) U.S. Cl.
CPC ........... *A61M 25/002* (2013.01); *A61B 50/20* (2016.02); *A61B 50/22* (2016.02); *A61L 2/10* (2013.01);
(Continued)

(58) Field of Classification Search
CPC .... A47F 7/0021; A47F 7/0028; A47F 7/0035; A47L 13/512; A61B 50/13; A61B 50/20;
(Continued)

(56) References Cited

U.S. PATENT DOCUMENTS 1,584,101 A * 5/1926 Kovarik ................. A47G 25/12
211/63
2,522,477 A * 9/1950 Wexberg ................... A24F 9/14
224/567
(Continued)

FOREIGN PATENT DOCUMENTS

CH 638713 A * 10/1983 ............... B25H 3/04
EP 3011926 B1 7/2017

*Primary Examiner* — Joshua E Rodden
(74) *Attorney, Agent, or Firm* — Gardner, Linn, Burkhart & Ondersma LLP (57) ABSTRACT

A storage apparatus is provided for storage of elongate articles in a vertical orientation, such as for storage of flexible esophageal dilators. The storage apparatus includes a gripping element of flexible material supported at a support frame. The gripping element includes receiving slots or apertures aligned with the spaced holes in the rigid panel. The support frame may include a rigid support panel with a pattern of spaced holes corresponding to respective ones of the receiving apertures of the gripping element. The gripping element grips and holds elongate articles at respective receiving apertures to suspend the articles in a vertical orientation. The elongate articles are retained in the gripping element until a user exerts a removal force on the article to retrieve it from the storage apparatus. The support frame may be disposed inside of a container, such as a cabinet or drawer.

20 Claims, 8 Drawing Sheets

(51) Int. Cl.
*A61L 2/10* (2006.01)
*A61L 2/26* (2006.01)
*A61B 50/20* (2016.01)
*A61B 50/22* (2016.01)
*A61B 50/13* (2016.01)
*A61B 50/10* (2016.01)
*A61B 50/18* (2016.01)

(52) U.S. Cl.
CPC ............... *A61L 2/26* (2013.01); *A61M 29/00* (2013.01); *A61B 50/13* (2016.02); *A61B 2050/105* (2016.02); *A61B 2050/185* (2016.02); *A61L 2202/11* (2013.01); *A61L 2202/182* (2013.01); *A61L 2202/24* (2013.01)

(58) Field of Classification Search
CPC ............... A61B 50/22; A61B 2050/105; A61B 2050/185; A61L 2/10; A61L 2/26; A61L 2202/11; A61L 2202/24; A61L 2202/182; A61M 25/002; A61M 29/00; B25H 3/04; B25H 3/06
USPC ............ 211/60.1, 62, 63, 64, 65, 66, 68, 69, 211/69.1–69.9, 70, 70.1, 70.2, 70.3, 70.4, 211/70.5, 70.6, 70.7, 70.8, 85.13, 124
See application file for complete search history.

(56) References Cited

U.S. PATENT DOCUMENTS

| | | | | |
|---|---|---|---|---|
| 2,956,687 | A * | 10/1960 | Robichaud | B65D 81/1075 206/217 |
| 3,004,270 | A * | 10/1961 | Cowley | B23G 5/04 408/239 R |
| 3,063,569 | A * | 11/1962 | Huber | A47L 13/512 211/89.01 |
| 3,365,761 | A * | 1/1968 | Kalvig | B25H 3/04 248/314 |
| 3,603,551 | A * | 9/1971 | Peterson | B25H 3/04 248/314 |
| 3,709,429 | A * | 1/1973 | Mckenzie | B04B 5/0414 211/74 |
| D274,964 | S | 8/1984 | Gioia | |
| 4,496,522 | A | 1/1985 | McConnell | |
| 4,597,496 | A * | 7/1986 | Kaplan | B25H 3/04 211/89.01 |
| 4,748,007 | A | 5/1988 | Gaudion et al. | |
| D298,893 | S | 12/1988 | Schwartz | |
| 4,807,421 | A * | 2/1989 | Araki | A23L 3/04 269/254 R |
| D303,191 | S | 9/1989 | Schwartz | |
| 4,905,951 | A * | 3/1990 | Putness | B25H 3/04 248/113 |
| 5,225,160 | A | 7/1993 | Sanford et al. | |
| 5,255,799 | A * | 10/1993 | Haynes | A63D 15/10 248/231.71 |
| 5,265,950 | A * | 11/1993 | Atkinson | A47B 81/005 211/64 |
| 5,267,660 | A * | 12/1993 | Kwon | A63B 55/40 206/315.6 |
| 5,415,287 | A | 5/1995 | Hamano et al. | |
| 5,454,931 | A * | 10/1995 | Lauve, Jr. | F41A 23/18 312/265.5 |
| 5,918,490 | A * | 7/1999 | Lion | A63B 55/408 206/315.3 |
| 5,996,818 | A * | 12/1999 | Boje | A47F 7/0028 422/549 |
| 6,641,781 | B2 | 11/2003 | Walta | |
| 6,814,932 | B2 | 11/2004 | Hlebovy et al. | |
| 6,884,392 | B2 | 4/2005 | Malkin et al. | |
| 7,061,597 | B2 | 6/2006 | Oberleitner et al. | |
| 7,138,087 | B1 | 11/2006 | Malkin et al. | |
| D539,423 | S | 3/2007 | Elsie | |
| 7,204,374 | B2 * | 4/2007 | Marek | B25H 3/04 211/70.6 |
| 7,651,672 | B2 | 1/2010 | Lin et al. | |
| 8,414,471 | B2 | 4/2013 | Mandava et al. | |
| 8,591,668 | B2 | 11/2013 | Pieroni et al. | |
| 8,757,737 | B2 | 6/2014 | Smart | |
| 8,992,416 | B2 | 3/2015 | Mandava et al. | |
| 9,348,013 | B2 | 5/2016 | Rahim et al. | |
| 9,439,992 | B2 | 9/2016 | Webb et al. | |
| 9,522,043 | B1 | 12/2016 | Hoftman et al. | |
| 9,566,127 | B1 | 2/2017 | Guezuraga et al. | |
| 9,724,439 | B2 | 8/2017 | Webb et al. | |
| 9,808,545 | B2 | 11/2017 | Mauzerall et al. | |
| 9,833,524 | B2 | 12/2017 | Mauzerall et al. | |
| 9,877,574 | B1 * | 1/2018 | Chih | A46B 17/02 |
| 9,962,230 | B2 | 5/2018 | Moe et al. | |
| 10,034,400 | B2 | 7/2018 | Rahim et al. | |
| 10,111,972 | B2 | 10/2018 | Mauzerall et al. | |
| 10,166,305 | B2 | 1/2019 | Mauzerall et al. | |
| 10,188,483 | B1 | 1/2019 | Bui | |
| 10,463,441 | B2 | 11/2019 | Tate et al. | |
| 10,525,156 | B1 | 1/2020 | Bui | |
| 10,617,288 | B2 | 4/2020 | Carlson | |
| 10,675,118 | B2 | 6/2020 | Yang et al. | |
| 10,816,025 | B1 * | 10/2020 | Su | B25B 23/02 |
| 11,197,732 | B2 | 12/2021 | Het Lam et al. | |
| 2004/0140280 | A1 * | 7/2004 | Cleveland | A47B 46/00 211/64 |
| 2006/0235268 | A1 | 10/2006 | Elsie et al. | |
| 2006/0283820 | A1 * | 12/2006 | Peters | A47B 81/005 211/64 |
| 2010/0182368 | A1 * | 7/2010 | Matsui | B41J 11/02 206/563 |
| 2011/0016027 | A1 | 1/2011 | Omura et al. | |
| 2011/0296800 | A1 * | 12/2011 | Clark | B65D 5/503 53/443 |
| 2015/0284018 | A1 | 10/2015 | Krosney | |
| 2016/0095432 | A1 * | 4/2016 | Wirthlin | A47B 81/005 211/64 |
| 2016/0113716 | A1 | 4/2016 | Bjorum et al. | |
| 2017/0224858 | A1 * | 8/2017 | Stibich | A61L 2/16 |
| 2018/0049834 | A1 | 2/2018 | Awadu | |
| 2019/0060494 | A1 | 2/2019 | Mauzerall et al. | |
| 2019/0090973 | A1 | 3/2019 | Het Lam et al. | |
| 2020/0107905 | A1 | 4/2020 | Yang et al. | |
| 2020/0118674 | A1 | 4/2020 | Le et al. | |
| 2020/0230272 | A1 * | 7/2020 | Foote | A61L 2/24 |
| 2020/0345452 | A1 | 11/2020 | Hooper et al. | |
| 2021/0022589 | A1 | 1/2021 | Crotti | |
| 2021/0077640 | A1 | 3/2021 | Mauzerall et al. | |
| 2022/0218854 | A1 * | 7/2022 | Preminger | A61L 2/10 |

* cited by examiner

STORAGE APPARATUS FOR ELONGATE ARTICLES

CROSS REFERENCE TO RELATED APPLICATION

The present application claims priority of U.S. provisional application Ser. No. 62/901,941 filed Sep. 18, 2019, which is hereby incorporated herein by reference in its entirety.

FIELD OF THE INVENTION

The present invention relates to apparatuses for storing and organizing medical implements.

BACKGROUND OF THE INVENTION

In the medical field, storage of elongate articles, such as flexible esophageal dilators, is typically accomplished using horizontally oriented trays, such that the elongate articles are stored in a horizontal orientation. The horizontal trays typically include parallel vertical dividers to allow separate articles to be stored without contacting other articles. Flexible esophageal dilators require support along substantially their entire length when stored in a horizontal orientation, due to their flexibility and weight, which can exceed several pounds. Concerns with storage of elongate articles for use in the medical field include the risk of contamination and the need to provide a sterile storage environment. One of the problems with conventional horizontally oriented trays is that the stored articles are in constant contact with the horizontal support surface, which increases the risk of contamination along the entire contact area.

SUMMARY OF THE INVENTION

The present invention provides a storage apparatus for elongate articles, such as medical dilators, to provide a convenient storage environment that maintains separation of the articles from other surfaces and other elongate articles. The storage apparatus provides a suspension system for storing elongate articles in a vertical orientation to reduce contamination and reduce the risk of infection to patients. The storage apparatus includes one or more support frames or cassettes for storage of elongate articles. Each support frame includes a rigid bottom support panel having a row of spaced openings, each opening capable of receiving a respective elongate article so that each article is spaced without contacting other stored elongate articles. Each spaced opening includes a gripping element made from a flexible medium for accepting an elongate article and gripping and securing the elongate article. The gripping element allows a user to place, secure, and store the elongate article with a simple vertical insertion motion, and to then subsequently remove that elongate article by exerting a removal force on the article with a vertical removal motion in the opposite direction. The flexible material of the gripping element is sufficiently rigid and exhibits a sufficiently high coefficient of friction to hold the elongate article against gravitational loads, and is sufficiently flexible to allow the elongate article to be removed with a pulling force in a downward motion relative to the support frame and gripping element.

According to one form of the present invention, a storage apparatus for vertical storage of a plurality of elongate articles includes a flexible gripping element supported at a support frame. The gripping element is provided for gripping and securing one end of an elongate article, allowing the opposite end to hang freely in a vertical orientation. A pattern of receiving apertures, such as in the form of a pattern of slits or openings, are formed in the gripping element to allow an elongate article to enter into the gripping element at each aperture, such that the flexible material of the gripping element frictionally engages the outside of the elongate article. The support frame may include a bottom support panel with a pattern of holes arranged along the support panel generally corresponding in size and location to the apertures formed in the gripping element, such that an elongate article can pass through the hole and into the respective aperture of the gripping element.

In one aspect, the support frame includes the bottom support panel, a top plate member, and two side plate members defining a hollow elongate rectangular frame. The support panel, top member, and side members are mechanically fastened such that the support frame is sufficiently rigid to support the weight of a plurality of elongate articles. A securing plate may be provided on top of the gripping element in order to secure the gripping element within the support frame such that, except for regions immediately surrounding the apertures, the gripping element does not move relative to the support frame during insertion of the elongate articles into the apertures of the gripping element. Optionally, the securing plate and gripping element are removable from the support frame through an open end of the support frame allowing the flexible gripping element to be removed for cleaning or replacement.

In another aspect, a plurality of slideably mounted rails are disposed inside an enclosed container, such as a wheeled cabinet or a wall-mounted cabinet. Each slideably mounted rail is mounted to the interior of the enclosed container. Each slideably mounted rail supports one of the support frames with a respective flexible gripping element for storing elongate articles in a vertical orientation.

According to yet another aspect, the storage apparatus is configured to be mounted inside an enclosed container in a fixed location, such as in a floor-mounted cabinet or along a vertical surface, such as a wall. The vertical surface mounted storage apparatus includes a main frame that supports the support frame with the flexible gripping element. A door frame and door are hingedly mounted onto the main frame. Another support frame with a flexible gripping element is mounted onto the door. The wall-mounted storage apparatus is configured so that elongate articles supported in the door's support frame do not contact or interfere with elongate articles supported in the main frame's support frame when the door is closed.

In still another aspect, the storage apparatus includes an ultraviolet light source on the interior of the storage apparatus to kill biological pathogens on the stored elongate articles, the interior structures of the storage apparatus, and in the air inside the storage apparatus. For example, such pathogens may include bacteria, viruses, mold, and the like.

Therefore, the present invention provides a storage apparatus for vertical storage of elongate articles with only limited contact with other surfaces, in a manner that facilitates convenient removal of elongate articles for use, and for replacement of the articles for storage after use and subsequent cleaning. The storage apparatus preferably includes a storage frame or cassette for supporting a flexible gripping element. The flexible gripping element has a defined pattern of slits or openings in spaced arrangement along the element. The material defining the slits or openings is configured to grip the elongate articles and secure the elongate articles for vertical storage.

These and other objects, advantages, purposes, and features of the present invention will become apparent upon review of the following specification in conjunction with the drawings.

DESCRIPTION OF THE PREFERRED EMBODIMENTS

Figure 1:
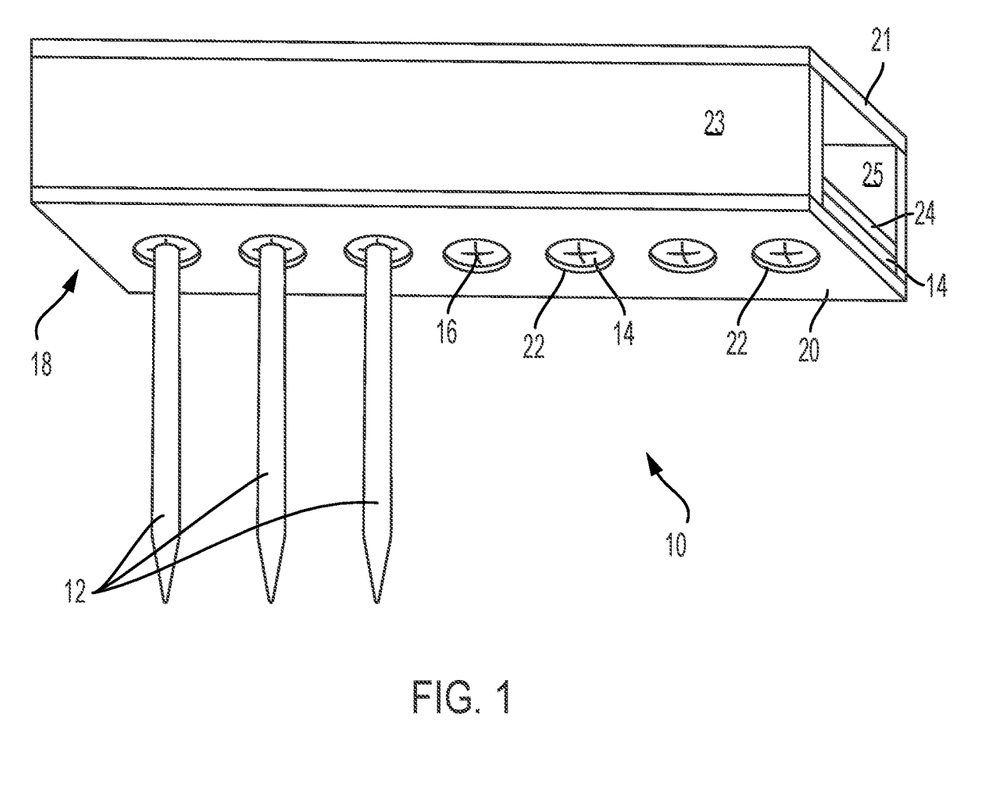
FIG. 1 is a perspective view of a vertical storage system for hanging elongate articles, in accordance with the present invention.
Figure 2:
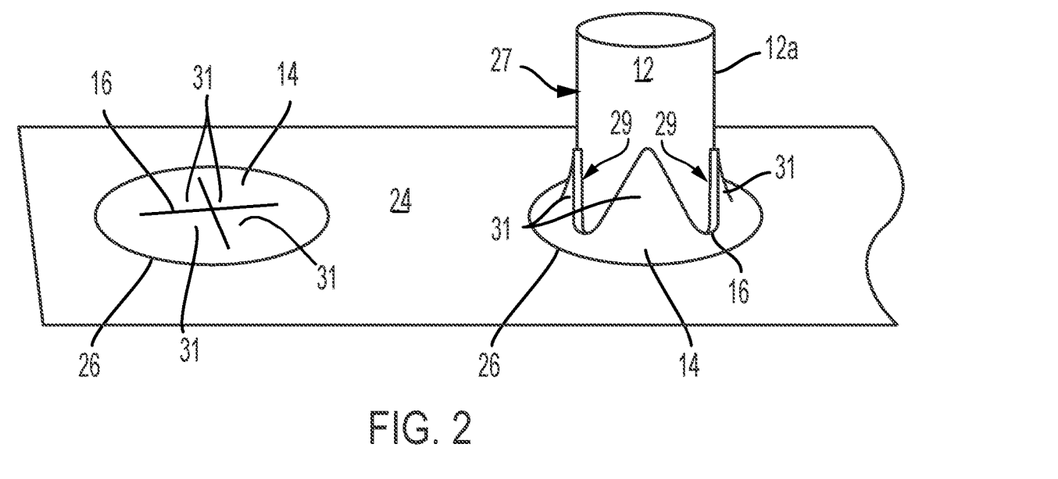
FIG. 2 is an enlarged perspective view of a portion of a support frame with a gripping element of the vertical storage system.

Referring now to the drawings and the illustrative embodiments depicted therein, a vertical storage system 10 provides for vertical storage of elongate articles 12, such as esophageal dilators (FIG. 1). The storage system 10 includes a gripping element 14 in the form of a flexible sheet material having a plurality of receiving slots or apertures 16 for gripping and statically holding elongate articles 12. The gripping element 14 is supported by a support cassette or support frame 18. The support frame 18 includes a hollow elongate rectangular frame defined by a rigid bottom support panel 20, a top plate 21, a first side plate 23, and a second side plate 25. The support panel 20, top plate 21, and side plate 23, 25, are mechanically fastened such that the support frame 18 is sufficiently rigid to support the weight of a plurality of elongate articles 12. The bottom support panel 20 of support frame 18 includes a pattern of holes 22 linearly spaced along the length of the panel 20. The gripping element 14 rests on the top of the support panel 20 and is held in position by a securing plate 24 which is positioned on top of the gripping element 14 so that the gripping element 14 is held between bottom support panel 20 and securing plate 24 (FIGS. 1 and 2). Like support panel 20, the securing plate 24 defines a pattern of holes 26, each of the holes 26 generally corresponding to the location of holes 22 of the bottom support panel 20 (FIGS. 2 and 3), and the holes 22, 26 corresponding to the locations of apertures 16 formed in the gripping element 14. The securing plate 24 may be removable from the support frame 18 in order to remove and clean or replace the gripping element 14. The support frame 18 may be made of metal, plastic, composite, or other rigid material suitable for sterile storage.

Figure 3:
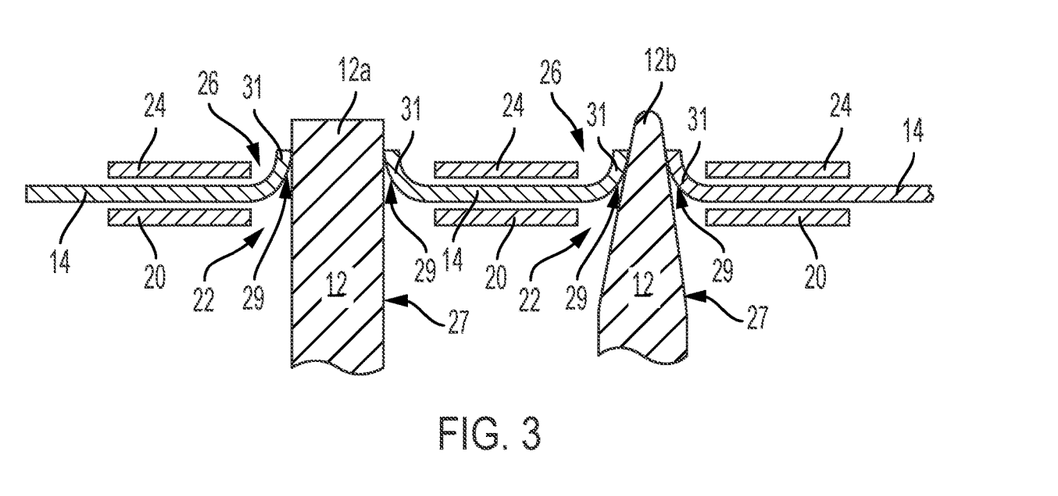
FIG. 3 is a cross-sectional view of a portion of the support frame and gripping element of the vertical storage system of FIG. 1.

Patterns of gripping slots or apertures 16 are cut or formed into the gripping element 14 and each aperture 16 defines a plurality of gripping fingers 31 (FIGS. 2 and 3). The receiving apertures 16 are disposed such that their centers are substantially aligned with the centers of the holes 22 of the rigid support panel 20 and the holes 26 of the securing plate 24, thus allowing end portions of the elongate articles 12 to pass through the bottom support panel 20, through openings formed by the apertures 16 in the gripping element 14, and through the securing plate 24.

The receiving apertures 16 are each configured to allow one of the elongate articles to at least temporarily form an opening in the gripping element 14 due to an entry or insertion force, causing the gripping fingers 31 to give way around the elongate article 12. The gripping fingers 31 of the gripping element 14 then grip or frictionally engage around the elongate article 12, thus providing a friction interaction between the exterior 27 of the elongate article 12 and exterior surfaces 29 of the gripping fingers 31, such as shown in FIGS. 2 and 3. The material of the gripping element 14 is sufficiently stiff and provides sufficient friction force between the gripping fingers 31 and the elongate article 12 to support the full weight of the suspended article 12, substantially without crushing or piercing or otherwise permanently deforming or damaging the structure of the elongate article 12.

As best shown in FIGS. 1 and 2, the receiving apertures 16 of the illustrated embodiment are formed by selectively opening a cruciform or cross pattern of slits cut into the gripping element 14, although it will be appreciated that the apertures 16 may be formed with different patterns, such as circles, rectangles, triangles, squares, cruciform, star patterns, or the like. The receiving apertures 16 are capable of accommodating various sizes of elongate articles 12, including a constant-diameter tail end 12a of an elongate article 12 and a tapered leading end 12b of an elongate article, such as shown in FIG. 3. The apertures 16 may be a slit pattern having substantially no void or opening in its relaxed or non-deflected state when not engaged by an elongate article (see the left side aperture in FIG. 2 and the right side apertures in FIG. 1) such that a void or opening in the receiving apertures 16 is first created during insertion of the elongate article 12. However, it is further envisioned that the apertures may have some initial width or separation between the adjacent gripping fingers, and/or that other shapes of non-slotted openings may be used, without departing from the spirit and scope of the present invention.

The flexible sheet material of gripping element 14 may be composed of rubber, plastic, composite, silicone, or similar flexible material, and preferably a material approved by the U.S. Food and Drug Administration (FDA) for medical use, optionally with antimicrobial properties. The flexible sheet material of gripping element 14 preferably has physical properties including sufficient surface friction to grip the exterior of an elongate article 12, being cleanable by cleaning solutions commonly used for reusable medical devices without absorbing the cleaning solutions, resistance to permanent deformation, readily elastically deformable, resistance to tearing, resistance to moisture absorption, resistance to degradation in the presence of ultraviolet (UV) light, and the like. It will be appreciated that the gripping element 14 may be formed of a uniform material throughout or may be formed of a composite of materials, such as various grades of silicone, or a combination of plastic and silicone, etc. For example, the peripheral regions of the gripping element 14 may be a rigid plastic while the gripping element portions on the central region of the element 14 may be flexible silicone, wherein the flexible silicone is mechanically or chemically coupled to the rigid plastic. It will also be appreciated that the gripping element 14 may be self-supporting within the support frame 18, such that the rigid bottom support panel 20 may be omitted. For example, the gripping element 14 may have sufficient structural rigidity to support its own weight and the weight of the elongate articles engaged with the element 14, while still allowing for a user to remove or insert elongate articles into the receiving apertures 16.

Figure 4:
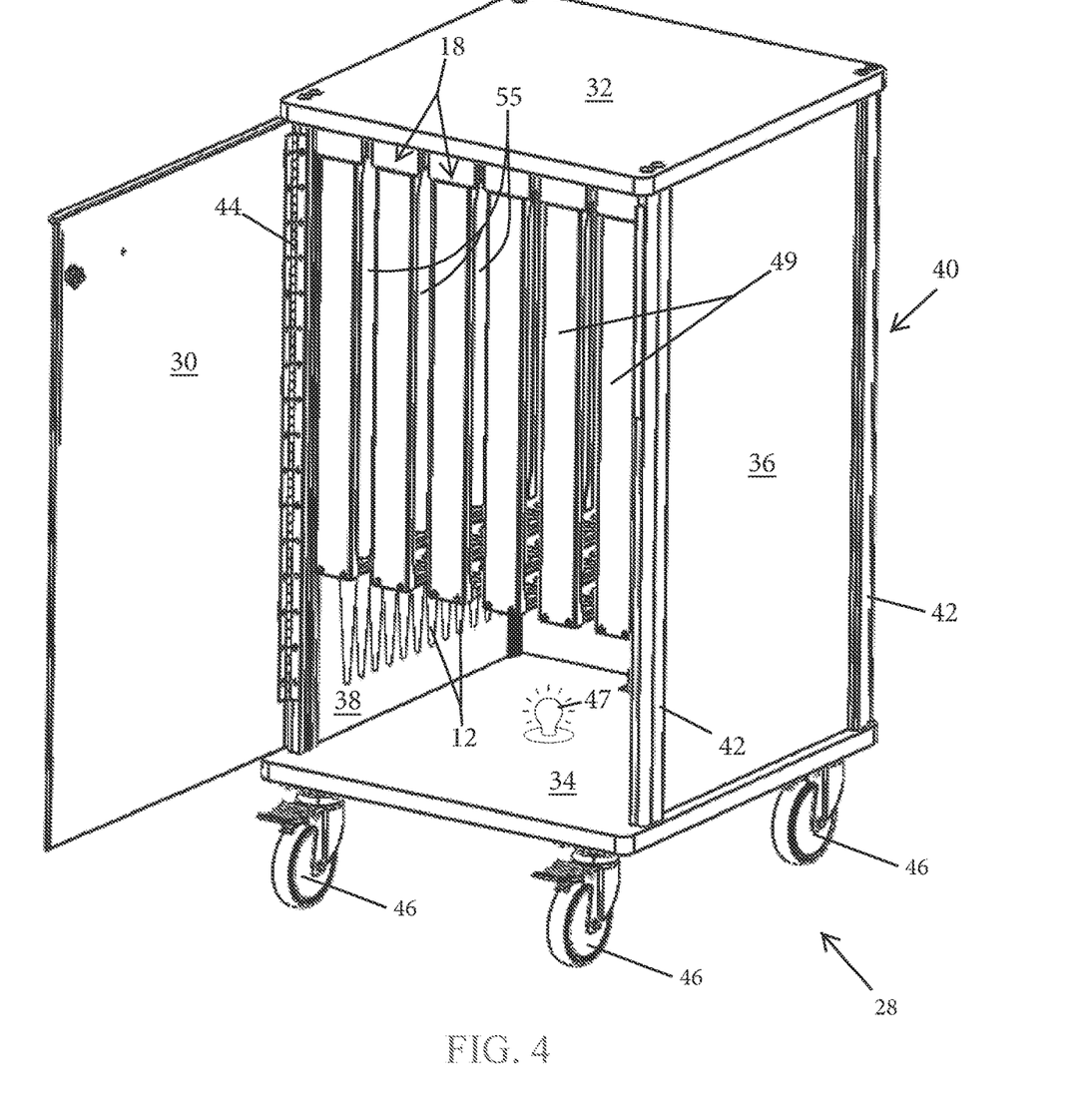
FIG. 4 is a perspective view of a cabinet supporting a plurality of the vertical storage systems of FIG. 1, in accordance with the present invention.

In the embodiment of FIG. 4, a plurality of support frames 18 are disposed inside a portable cabinet 28 having a door 30, a top panel 32, a bottom panel 34, a right side panel 36, a left side panel 38, and a back panel 40, all cooperating to define the cabinet 28. Optionally, and as shown, a plurality of frame members 42 form a frame of the cabinet 28, with each frame member 42 coupled between the top panel 32 and the bottom panel 34, with the right side panel 36, the left side panel 38, and the back panel 40 disposed between the frame members 42. Optionally, the side panels 36 and 38 and the back panel 40 may be attached to the exterior side of the frame members 42. The door 30 is mounted by a hinge 44, which is fixed to either the edge of the left side panel 38, right side panel 36, or a frame member 42. The cabinet 28 is supported by locking wheels 46 attached to the bottom of the bottom panel 34 to allow the cabinet to be maneuvered, such as from one operating room to another operating room.

Figure 5:
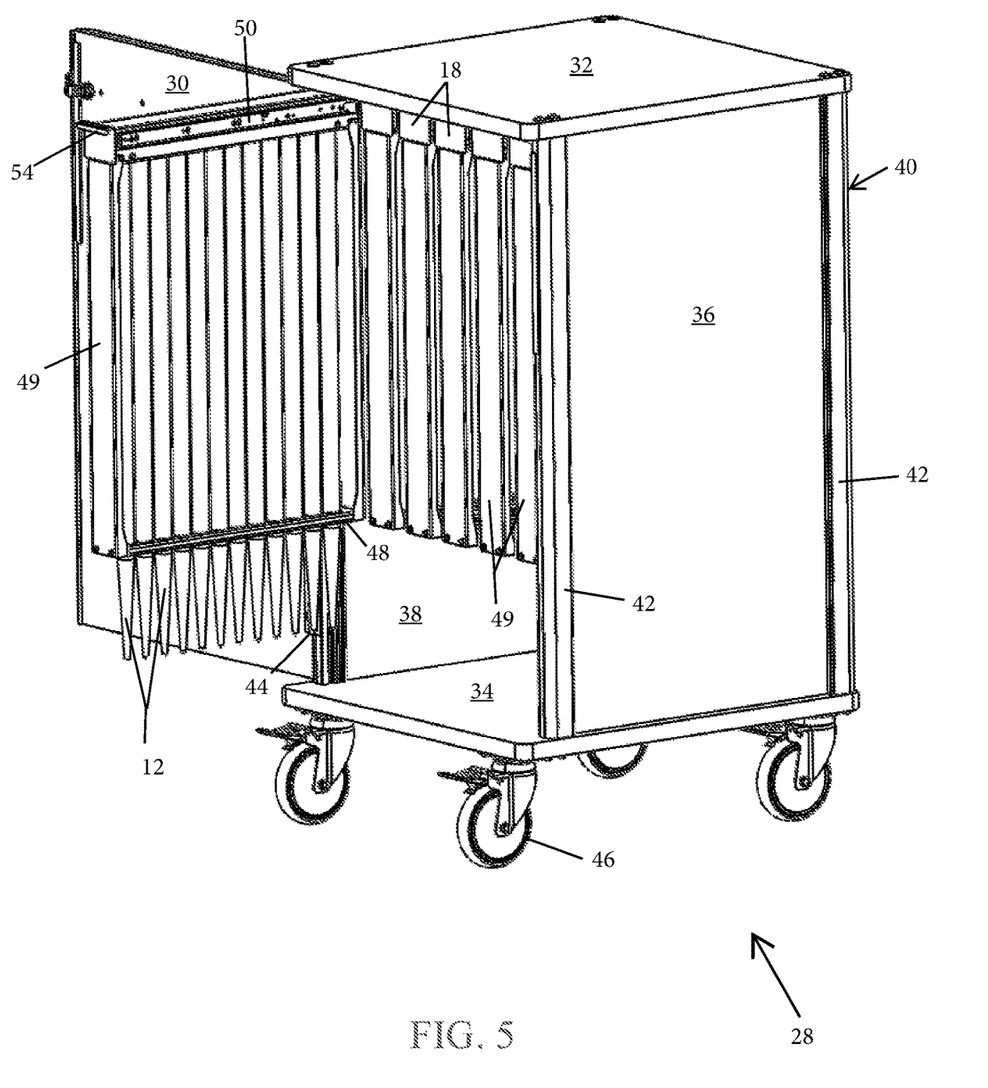
FIG. 5 is another perspective view of the cabinet and vertical storage systems of FIG. 4, shown with one of the support frames extended from the cabinet.
Figure 6:
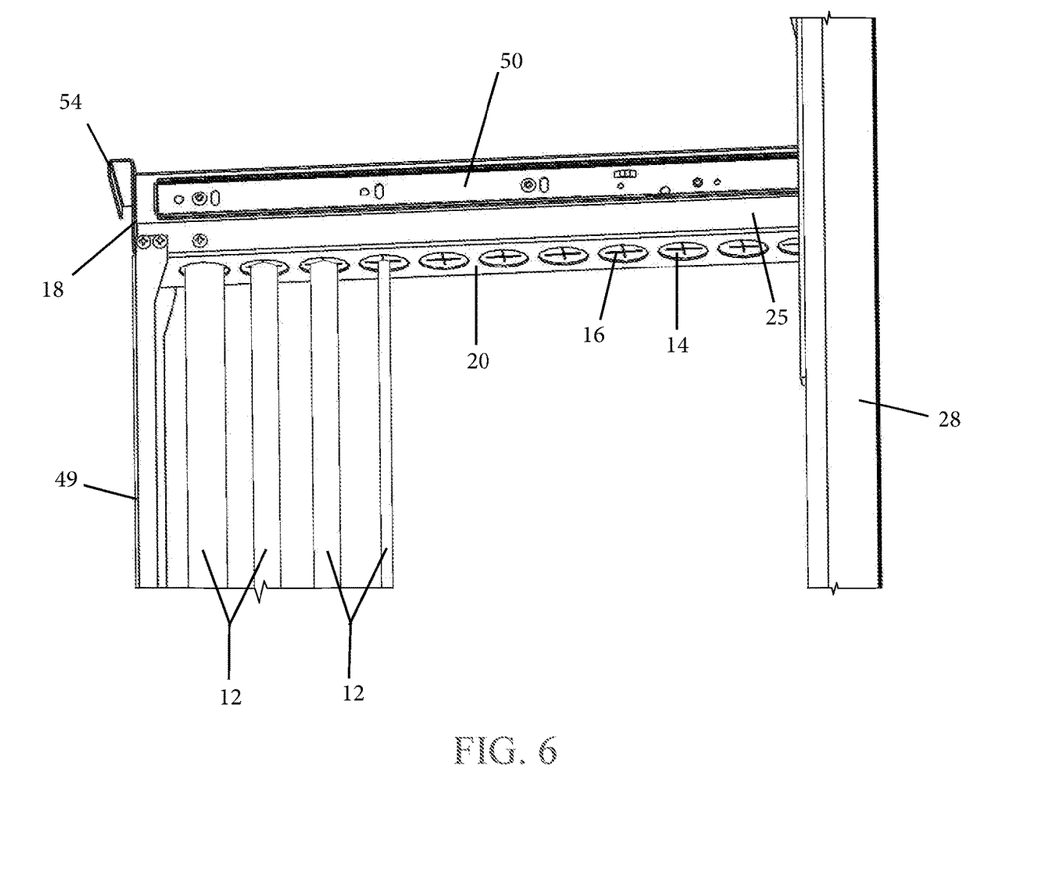
FIG. 6 is an enlarged perspective view of the extended support frame of FIG. 5.
Figure 7:
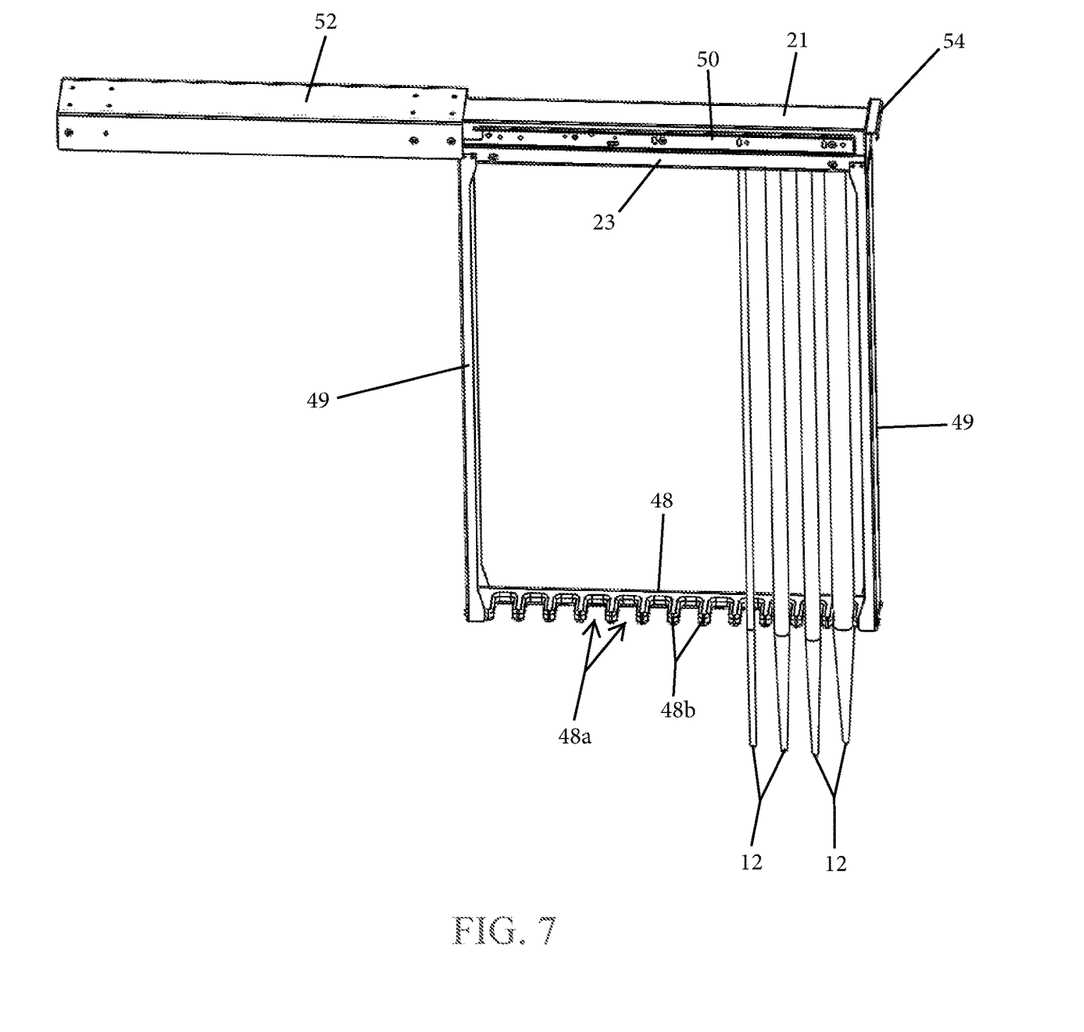
FIG. 7 is a perspective view of a vertical storage system of FIG. 1 supported by a slidable mounting rail engaged with a fixed mounting rail, in accordance with the present invention.

The support frames 18 within cabinet 28 may be slideably supported by slidable mounting rails 50 that are mechanically fixed onto each side of the support frame 18 (FIGS. 5 and 6). The slidable rails 50 enter into respective fixed mounting rails 52 (FIG. 7) that are mechanically fixed within the cabinet 28, thus enabling the support frame 18 to be slid outward relative to the cabinet 28, such as shown in FIG. 5. The fixed rails 52 are mechanically attached within the cabinet 28 at the bottom surface of the top panel 32. The sliding rails 50 are configured such that when the door 30 is in an open position the support frame 18 may slide out of the opening exposed by the open door to allow access to all elongate articles 12 stored on that frame, such as shown in FIG. 6. The support frames 18 within cabinet 28 each include an end plate handle 54 attached to the front of the support frame, to allow a user to pull the slideably mounted support frame 18 outward from the cabinet 28. The support frames 18 each include a lower divider 48 configured to provide separation between the suspended ends of elongate articles 12 stored on the respective support frames 18. The lower divider 48 is supported by vertical supports 49, one vertical support 49 connected to each end of the support frame 18 as shown in FIG. 7. The lower divider 48 has a plurality of divided openings 48a defined by a plurality of horizontal dividing fingers 48b. Optionally, vertical divider sheets or screens 55 (FIG. 4) may be disposed between support frames 18 and lower dividers 48 to ensure separation of the articles 12 even while moving the cabinet 28.

Figure 8:
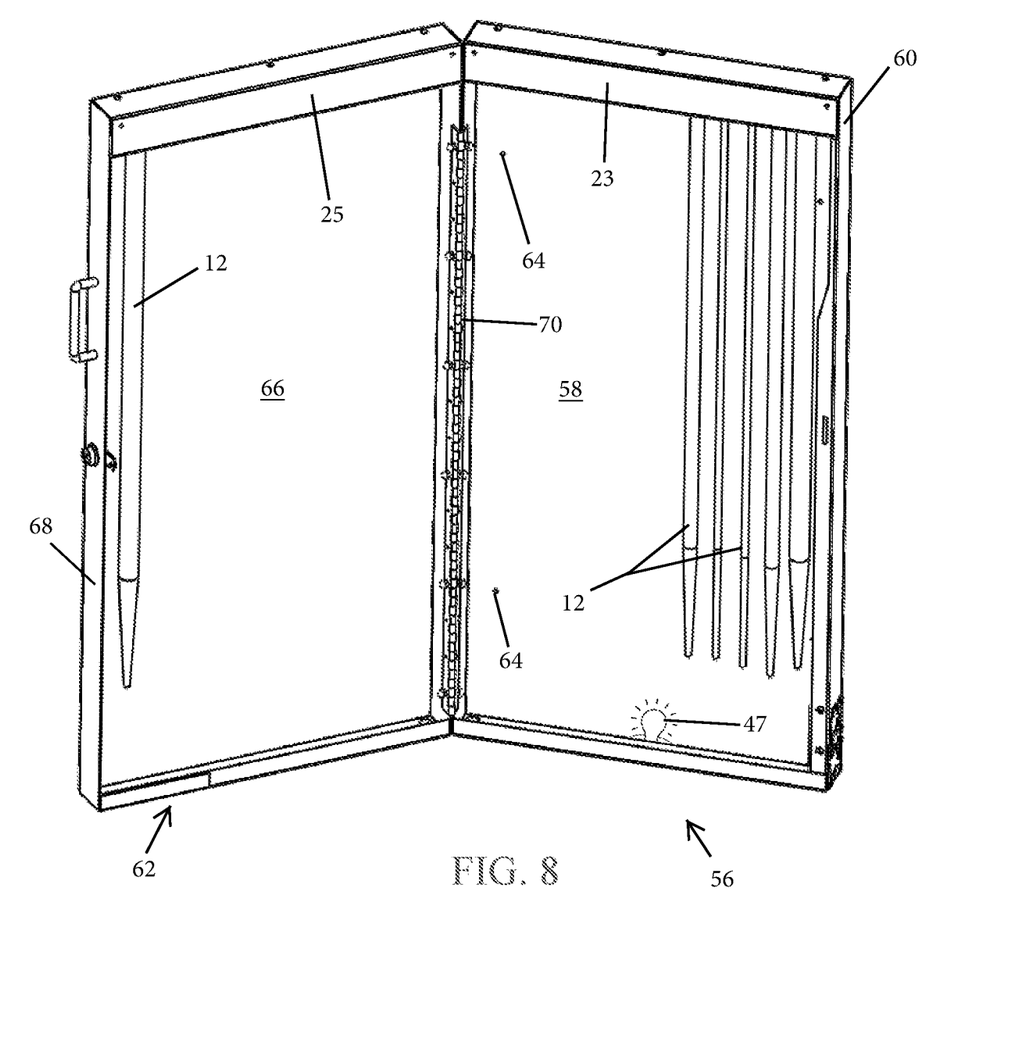
FIG. 8 is a perspective view of a wall-mountable cabinet supporting a plurality of the vertical storage systems of FIG. 1, in accordance with the present invention.
Figure 9:
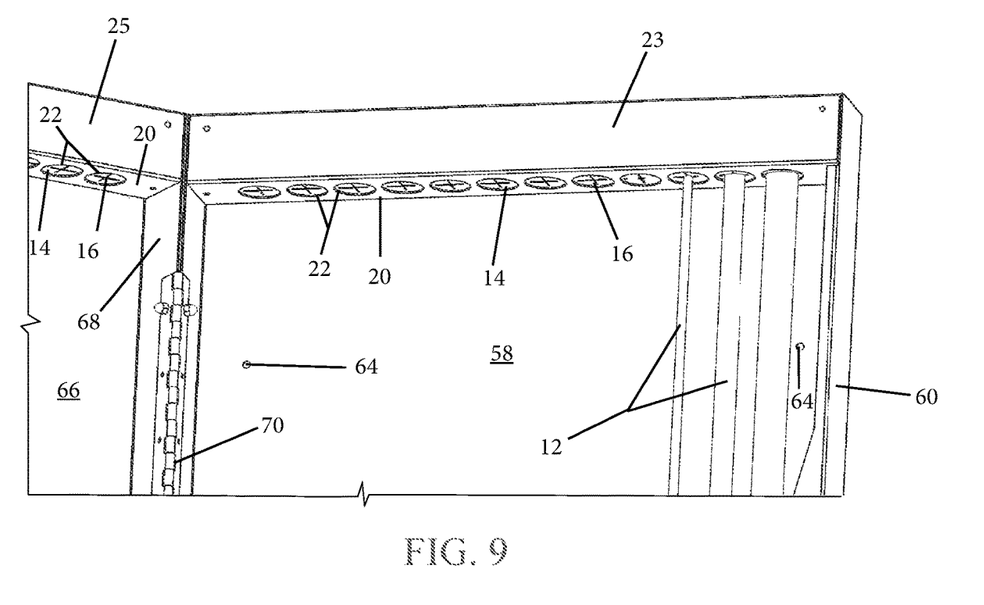
FIG. 9 is an enlarged perspective view of an upper region of the cabinet of FIG. 8.

In another embodiment, a vertical surface-mountable cabinet 56 supports a set of two support frames 18, such as shown in FIGS. 8 and 9. The cabinet 56 includes a rear panel 58, a rectangular main frame 60, and a hingedly mounted door 62 (FIG. 8). The rear panel 58 includes mounting holes 64 that facilitate mounting the cabinet 56 to a vertical surface, such as a wall. The door 62 includes a door panel 66 and a rectangular door frame 68. The door 62 is fixed to the main frame 60 with a vertically oriented hinge 70. A support frame 18 is fixedly mounted to the top of the main frame 60 to provide vertical storage of elongate articles 12 (FIGS. 8 and 9). Another support frame 18 is fixedly mounted to the top of the door frame 68 to provide vertical storage of additional elongate articles 12, such that the door-mounted support frame 18 and the other support frame 18 that is mounted on the main frame 60 reduce the likelihood of contact or interference of the stored elongate articles 12 when the door is open, closed, or moving between opened and closed positions.

Disinfecting elements, such as a disinfecting light 47, may be provided for use with the storage system 10, such as mounted on the interior of the portable cabinet 28 (FIG. 4) or on the interior of the cabinet 56 (FIG. 8). The disinfecting elements provide infection and contamination control of the stored elongate articles 12. Disinfecting elements may emit ultraviolet light (less than about 400 nm wavelength) or violet or near-ultraviolet light (about 405 nm wavelength). The disinfecting elements are provided for destroying biological pathogens on the stored elongate articles, the interior structures of the storage apparatus, and in the air within the storage apparatus. Such pathogens may include bacteria, viruses, mold, and the like. The disinfecting light may include an individual bulb, as shown, or may include a string or strand of multiple lights, or one or more tubular elongate lights.

Accordingly, the vertical storage system of the present invention provides vertical storage for elongate articles, such as medical dilators. The storage system provides a simple and effective storage solution for elongate articles, for keeping the dilators clean, orderly, and readily removable and replaceable. The storage system includes a flexible sheet of material having receiving slots or apertures that form fingers or edges to grip the exterior of an elongate article with sufficient gripping force to maintain each article in a vertical orientation until it is removed by a downward pulling force. The gripping force is accomplished via the gripping fingers or elements at the aperture pattern and the physical properties of the flexible material, such as elastic deformability and exterior friction coefficient. The storage device may be disposed inside a container for convenient access, transportation, and protection from contamination. The storage device may also include disinfecting lights to further decrease contaminants on the stored elongate articles.

Changes and modifications in the specifically described embodiments can be carried out without departing from the principles of the present invention, which is intended to be limited only by scope of the appended claims, as interpreted according to the principles of patent law, including the doctrine of equivalents.

The embodiments of the invention in which an exclusive property or privilege is claimed are defined as follows:

1. A storage apparatus for storing elongate articles in a vertical orientation, said storage apparatus comprising:
   a container comprising a top panel, a bottom panel, a pair of side panels, a back panel, and an openable door, which cooperate to define an interior;
   at least one mounting rail coupled to said top panel in said interior of said container;
   at least one support frame coupled to said mounting rail, said support frame defining an enclosed support chamber sized and configured to receive respective upper portions of a plurality of the elongate articles, wherein said support frame is moveable along said mounting rail between retracted and extended positions relative to said interior when said openable door is open;
   a gripping element at a lower region of said support frame and spaced below said mounting rail, said gripping element comprising a sheet of flexible material having a plurality of receiving apertures in spaced arrangement, said gripping element configured to suspend the plurality of elongate articles in a vertical orientation and in horizontally spaced arrangement; and said gripping element configured to permit the respective upper portions of the elongate articles to pass upwardly through said flexible material at respective ones of said receiving apertures such that said gripping element releasably grips the upper portions of the elongate articles at the respective gripping apertures such that the elongate articles are retained in said gripping element until a user exerts a removal force on a selected one of the elongate articles;

wherein said gripping element is configured to support the full weight of each of the elongate articles at the upper portions such that lower ends of the elongate articles hang freely with the elongate articles in the vertical orientation.

2. The storage apparatus of claim 1, wherein each of said receiving apertures comprises a hole formed through said gripping element, said hole comprising one chosen from a circular hole, a square hole, a rectangular hole, a triangular hole, a cruciform shaped hole, and a star shaped hole.

3. The storage apparatus of claim 1, wherein each of said receiving apertures is defined by a slit pattern formed through said gripping element, said slit pattern having no voids when in a non-deflected state.

4. The storage apparatus of claim 3, wherein said slit pattern comprises a cruciform slit pattern defining a plurality of wedge shaped gripping fingers in said gripping element, said gripping fingers configured to deform around the exterior of the elongate article.

5. The storage apparatus of claim 1, wherein said support frame comprises a rigid bottom support panel defining a plurality of panel openings in spaced arrangement and a rigid top securing plate defining a plurality of plate openings in spaced arrangement, said bottom support panel configured to support said gripping element and said securing plate configured to retain said gripping element relative to said bottom support panel, wherein said plurality of receiving apertures of said gripping element are substantially aligned with respective ones of said panel openings and said plate openings.

6. The storage apparatus of claim 1, comprising said at least one mounting rail including a plurality of said mounting rails and said at least one support frame including a plurality of said support frames, wherein said support frames are coupled to respective ones of said mounting rails, and said mounting rails are coupled to said top panel in parallel spaced arrangement.

7. The storage apparatus of claim 6, further comprising a plurality of dividers in spaced arrangement at the interior of said container, each of said dividers disposed between the elongate articles suspended at one of said support frames and the elongate articles suspended from an adjacent one of said support frames.

8. The storage apparatus of claim 1, further comprising a disinfecting light supported at the interior of said container and operable to reduce biological contamination on the elongate articles.

9. The storage apparatus of claim 1, wherein said gripping element is selectively removable from said support frame.

10. A storage cassette for vertically storing elongate articles, said storage cassette comprising:

a frame having a rigid bottom support panel and pair of side plates extending upwardly from said support panel, said support panel defining a plurality of panel openings in spaced arrangement, and said frame defining an enclosed support chamber above said support panel and configured to receive respective upper portions of a plurality of the elongate articles;

a gripping element removably supported at said support panel, said gripping element defining a plurality of receiving apertures in spaced arrangement, wherein said gripping element flexes upwardly at said receiving apertures to permit the elongate articles to pass upwardly through respective ones of said receiving apertures in a manner such that said enclosed support chamber receives the upper portions of the elongate articles and said gripping element frictionally engages and supports the elongate articles at said receiving apertures; and a top securing plate defining a plurality of plate openings in spaced arrangement, said securing plate securing said gripping element along said bottom support panel;

wherein respective ones of said receiving apertures of said gripping element, respective ones of said plate openings, and respective ones of said panel openings are aligned with one another; and wherein said frame and said gripping element are configured to support the full weight of each of the elongate articles and thereby suspend the elongate articles in a vertical orientation and in horizontally spaced arrangement such that lower ends of the elongate articles hang freely with the elongate articles in the vertical orientation.

11. The storage cassette of claim 10, wherein each of said receiving apertures comprises a hole formed through said gripping element, said hole comprising one chosen from a circular hole, a square hole, a rectangular hole, a triangular hole, a cruciform shaped hole, and a star shaped hole.

12. The storage cassette of claim 10, wherein each of said receiving apertures is defined by a slit pattern through said gripping element, said slit pattern having no voids when in a non-deflected state.

13. The storage cassette of claim 12, wherein said slit pattern comprises a cruciform pattern defining a plurality of wedge shaped gripping fingers, said gripping fingers configured to deform around the exterior of the elongate article.

14. The storage cassette of claim 10, further in combination with a container, wherein said storage cassette is supported at an interior of said container, and said storage cassette is moveable between a retracted position in said interior of said container, and an extended position at least partly outside of said interior of said container.

15. The storage system of claim 14, further comprising a disinfecting light supported at the interior of said container and operable to reduce biological contamination on the elongate articles suspended at said gripping element.

16. The storage cassette of claim 10, wherein said frame comprises a top plate coupled to said side plates and positioned directly above said support panel and said receiving apertures, wherein said top plate cooperates with said side plates and said support panel to enclose four sides of said support chamber.

17. A storage system for suspending elongate articles in a vertical orientation, said storage system comprising:

a container comprising a top panel, a bottom panel, a pair of side panels, a back panel, and an openable door that cooperate to define an interior;

a plurality of wheels coupled to said bottom panel;

a plurality of mounting rails coupled to said top panel in said interior of said container;

a plurality of cassettes coupled to respective ones of said mounting rails and moveable along said mounting rail between retracted and extended positions, each of said cassettes having a rigid bottom support panel and pair of side plates extending upwardly from said support panel to define an enclosed support chamber above said support panel and configured to receive upper portions of a plurality of the elongate articles, said support panel defining a plurality of panel openings in spaced arrangement wherein said cassettes are independently moveable along said mounting rails between retracted and extended positions relative to said interior when said openable door is open; and a gripping element at each of said support panels, each said gripping element comprising a sheet material defining a plurality of receiving apertures in spaced arrangement, wherein each said gripping element flexes upwardly at said receiving apertures to permit the elongate articles to pass upwardly through respective ones of said receiving apertures in a manner such that said gripping element frictionally engages and supports the elongate articles at said receiving apertures in a vertical orientation and in horizontally spaced arrangement;

wherein respective ones of said receiving apertures are aligned with respective ones of said panel openings; and wherein said cassettes and said gripping elements are configured to support the full weight of each of the elongate articles and thereby suspend the elongate articles such that lower ends of the elongate articles hang freely in said interior when said cassettes are in the retracted positions.

18. The storage system of claim 17, further comprising a rigid top securing plate positioned atop each said gripping element, said top securing plates each defining a plurality of plate openings in spaced arrangement and aligned with said panel openings and said receiving apertures.

19. The storage system of claim 17, wherein each of said receiving apertures is defined by a cruciform slit pattern forming a plurality of wedge shaped gripping fingers, said slit pattern having no voids when in a non-deflected state, and said gripping fingers configured to deform around the exterior of the elongate article.

20. The storage system of claim 17, wherein said cassette comprises a top plate coupled to said side plates and positioned directly above said support panel and said receiving apertures, wherein said top plate cooperates with said side plates and said support panel to enclose four sides of said support chamber.

* * * * *

UNITED STATES PATENT AND TRADEMARK OFFICE
CERTIFICATE OF CORRECTION

PATENT NO. : 11,872,353 B2
APPLICATION NO. : 17/025451
DATED : January 16, 2024
INVENTOR(S) : Justin M. Bjorum and Noel J. Bodkins It is certified that error appears in the above-identified patent and that said Letters Patent is hereby corrected as shown below:

In the Claims

Column 9
Line 14, Claim 17, insert --supported-- after "element"

Signed and Sealed this
Thirteenth Day of February, 2024

*Katherine Kelly Vidal*

Katherine Kelly Vidal
*Director of the United States Patent and Trademark Office*